(12) United States Patent
Citron

(10) Patent No.: US 8,686,209 B2
(45) Date of Patent: Apr. 1, 2014

(54) α-OLEFIN MANUFACTURING PROCESS

(75) Inventor: Joel David Citron, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 13/390,540

(22) PCT Filed: Aug. 17, 2010

(86) PCT No.: PCT/US2010/045741
§ 371 (c)(1),
(2), (4) Date: Feb. 15, 2012

(87) PCT Pub. No.: WO2011/022384
PCT Pub. Date: Feb. 24, 2011

(65) Prior Publication Data
US 2012/0157686 A1    Jun. 21, 2012

Related U.S. Application Data

(60) Provisional application No. 61/234,362, filed on Aug. 17, 2009.

(51) Int. Cl.
*C07C 2/32* (2006.01)
*C07C 2/08* (2006.01)

(52) U.S. Cl.
USPC .......................................... 585/523; 585/527

(58) Field of Classification Search
USPC ................................................ 585/523, 527
See application file for complete search history.

(56) References Cited

U.S. PATENT DOCUMENTS

| 6,103,946 A | 8/2000 | Brookhart et al. |
| 6,710,006 B2 | 3/2004 | De Boer et al. |

FOREIGN PATENT DOCUMENTS

WO    WO 2007059015    5/2007

OTHER PUBLICATIONS

Babik S T et al, "Propylene bulk phase oligomerization with bisiminepyridine iron complexes in a calorimeter: mechanistic investigation of 1,2 versus 2,1 propylene insertion", Journal of Organometallic Chemistry, vol. 683, No. 1, pp. 209-219 (Oct. 7, 2003).
Bianchini C et al, Ethylene oligomerization, homopolymerization and copolymerization by iron and cobalt catalysts with 2,6 (bis-organylimino)pyridyl ligands, Coordination Chemistry Reviews, Elsevier Science, vol. 250, No. 11-12, pp. 1391-1418, (Jun. 1, 2006).
Britovsek G J P et al:"Oligomerisation OfEthylene By Bis (Imino)Pyridyliron And -Cobalt Complexes", Chemistry—A European Journal, vol. 6, No. 12, pp. 2221-2231.(Jan. 1, 2000).
B. Cornils et al, Applied Homogeneous Catalysis with Organometallic Compounds, A Comprehensive Handbook, vol. 1 , VCH Verlagsgesellschaft mbH, Weinheim, 1996, p. 246-256.
B. Elvers, et al, Encyclopedia of Industrial Chemistry, vol. A13, VCH Verlagsgesellschaft mbH, Weinheim, 1989, p. 243-247 and 275-276.
Gorl et al, "Iron complexes with omega-alkenyl substituted bis(arylimino)pyridine ligands as catalyst precursors for the oligomerization and polymerization of ethylene" Journal of Molecular Catalysis. \a, Chemical, Elsevier, Amsterdam, vol. 273, No. 1-2, pp. 1818-132, (Jun. 29, 2007).
W. Hang et al, "Ethylene oligomerization by novel iron (II) diimine complexes/MAO" Chinese Science Bulletin, Science Pres, Beijing, Cn, vol. 47, No. 19, pp. 1616-1618 (Oct. 1, 2002).
Ionkin, et al, "Nitro-substituted iron (II) tidentate bis(imino)pyridine complexes as high temperature catalysts for the production of alpha olefins", Journal of Polymer Science. Part A, Polymer Chemistry, vol. 44, No. 8, pp. 2615-2638 (Jan. 1, 2006).
Ionkin, et al, "High-Temperature Catalysts for the Production of.alpha.-Olefins Based on Iron(II) and Cobalt(II) Tridentate Bis(imino)pyridine Complexes with a Double Pattern of Substitution:o-Methylplus o-Fluorine in the Same Imino Arm" Organometallics, 27(6), 1147-1156, (2008).
Ionkin,et al, "High-temperature catalysts for the production of .alpha.-olefins based on iron(II) and iron(III) tridentate bis(imino)pyridine complexes modified by nitrilo group" Journal of Polymer Science, Part a: Polymer Chemistry , 46(2),585-611,(2008).
International Search Report PCT/US2010/045741, mailed Aug. 11, 2010.

*Primary Examiner* — Caixia Lu

(57) ABSTRACT

In an α-olefin manufacturing process by the oligomerization of ethylene using an iron complex of a diimine of a 2,6-diacylpyridine or a 2,6-pyridinecarboxaldehyde, in which certain substituted iminoaryl groups are present, less higher molecular weight unwanted products are produced when the diimine and/or its precursor arylamine does not have impurities with substitution on a second ortho position to the imino group. This leads to less fouling of the process apparatus and higher yields of desired α-olefins.

8 Claims, No Drawings

α-OLEFIN MANUFACTURING PROCESS

SUMMARY OF THE INVENTION

A process for manufacturing α-olefins by oligomerization of ethylene is improved when the catalyst used, an iron complex of a diimine of a 2,6-diacylpyridine or a 2,6-pyridinedicarboxaldehyde, is made from particularly pure aromatic amines and/or purified before use to reduce certain types of impurities.

TECHNICAL BACKGROUND

α-Olefins (AOs) are important synthetic organic chemicals, being used widely as chemical intermediates and monomers for polymerizations. They are most commonly made by oligomerization of ethylene using transition metal containing or other types of catalysts, see for instance B. Elvers, et al., Ed. Ullmann's Encyclopedia of Industrial Chemistry, Vol. A13, VCH Verlagsgesellschaft mbH, Weinheim, 1989, p. 243-247 and 275-276, and B. Cornils, et al., Applied Homogeneous Catalysis with Organometallic Compounds, A Comprehensive Handbook, Vol. 1, VCH Verlagsgesellschaft mbH, Weinheim, 1996, p. 246-256. Catalysts that may be used include iron complexes of certain diimines of a 2,6-diacylpyridine or a 2,6-pyridinedicarboxaldehyde, see for instance U.S. Pat. No. 6,103,946. The apparent key factor in these complexes making AOs from ethylene instead of higher polymers is control of the steric hindrance about the iron atom, for instance by controlling the size of the aryl group which is of the imino groups, see George J. P. Britovsek, et al., *Chem. Eur. J.* vol. 6, p. 2221-2231 (2000), which is hereby included by reference. Typically these catalysts are very active, and under the proper conditions these catalysts produce a series of AOs of the general formula $CH_2=CH_2(CH_2CH_2)_nH$ wherein n is an integer of 1 or more. The relative concentrations of the various AOs produced are determined by the Schulz-Flory equation (SFE), for more details see below.

However it has been found that certain of these iron complexes, for instance those which are symmetrical in substitution of the aryl imino group, produce a mixture of AOs that deviates from the product distribution predicted by the SFE, producing higher amounts of relatively low molecular weight (MW) and higher MW AOs, see U.S. Pat. No. 6,710,006, which is hereby included by reference. While production of small amount of "excess" low MW AOs is not a serious problem, production of "excess" higher MW AOs can be, since they may precipitate from the process mixture and foul the reactor train.

As a solution to this problem the inventors of U.S. Pat. No. 6,710,006 found that similar unsymmetrically substituted ligands gave much better agreement with the SFE and decreased the amount of higher MW AOs produced. Formula (I) is an example of a symmetrical ligand from U.S. Pat. No. 6,710,006, while Formula (II) is an example of their improved ligand.

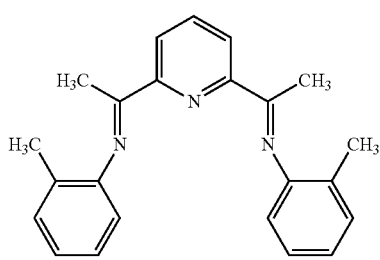

(I)

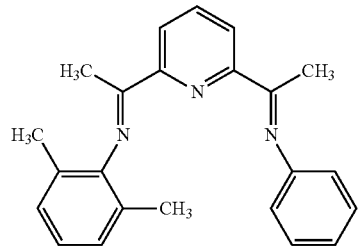

(II)

However, production of the unsymmetrical iron complexes such as (II) requires more steps and more careful purification of the resulting intermediate and final products, so overall yields of the iron complexes are relatively low, 6-17% reported in the three instances in U.S. Pat. No. 6,710,006. Since 2,6-diacylpyridines and 2,6-pyridinedicarboxaldehydes are expensive (for instance 2,6-diacetylpyridine from Aldrich-Sigma is $345.50 for 25 g as of Jul. 30, 2009), such catalysts are relatively expensive.

It would therefore be advantageous if more readily synthesized ligands (and their iron complexes) could be used without giving product mixtures which deviate from the SFE.

SUMMARY OF THE INVENTION

This invention concerns a process for the preparation of an improved symmetrical diimine of a 2,6-diacylpyridine or a 2,6-pyridinedicarboxaldehyde of the formula

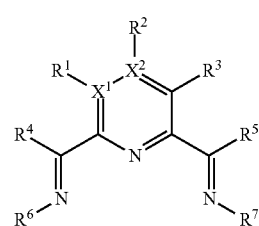

(III)

wherein:
$X^1$ and $X^2$ are each independently carbon or nitrogen;
$R^1$ and $R^2$ are each independently hydrogen, hydrocarbyl, substituted hydrocarbyl or a functional group, provided that when $X^1$ is nitrogen $R^1$ is not present, and when $X^2$ is nitrogen $R^2$ is not present;
$R^3$ is hydrogen, hydrocarbyl, substituted hydrocarbyl or a functional group;
$R^4$ and $R^5$ are each independently hydrogen, hydrocarbyl, or substituted hydrocarbyl;
$R^6$ and $R^7$ are the same, and are aryl groups in which a first ortho position is substituted by hydrocarbyl, substituted hydrocarbyl or a functional group, and a second ortho position is hydrogen or fluorine;
and provided that:
said symmetrical diimine of a 2,6-diacylpyridine or a 2,6-pyridinedicarboxaldehyde is made with a primary aromatic amine that contains no more than 0.5 mol percent of impurities which, impurities are themselves primary aromatic amines and in which one of said second ortho positions is not hydrogen or fluorine;
and wherein said mol percent is based on the total amount of primary aromatic amines present.

This invention also concerns an improved process for the oligomerization of ethylene to a series of α-olefins of formula $CH_2=CH_2(CH_2CH_2)_nH$ wherein n is an integer of 1 or more, using as all or part of the catalyst system an iron complex of a symmetrical diimine of a 2,6-diacylpyridine or a 2,6-pyridinedicarboxaldehyde of the formula:

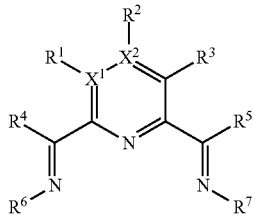

(III)

wherein:

$X^1$ and $X^2$ are each independently carbon or nitrogen;

$R^1$ and $R^2$ are independently hydrogen, hydrocarbyl, substituted hydrocarbyl or a functional group, provided that when $X^1$ is nitrogen $R^1$ is not present, and when $X^2$ is nitrogen $R^2$ is not present;

$R^3$ is hydrocarbyl, substituted hydrocarbyl, a functional group or hydrogen;

$R^4$ and $R^5$ are each independently hydrogen, hydrocarbyl, or substituted hydrocarbyl;

$R^6$ and $R^7$ are the same, and are aryl groups in which a first ortho position is substituted by hydrocarbyl, substituted hydrocarbyl or a functional group, and a second ortho position is hydrogen or fluorine;

wherein the improvement comprises:

said symmetrical diimine of a 2,6-diacylpyridine or a 2,6-pyridinedicarboxaldehyde is made with a primary aromatic amine that contains no more than 0.5 mol percent of impurities, which impurities are themselves primary aromatic amines and in which one of said second ortho positions is not hydrogen or fluorine;

and/or said symmetrical diimine of a 2,6-diacylpyridine or a 2,6-pyridinedicarboxaldehyde contains no more than 0.5 mol percent of diimines in which said one of said second ortho positions is not a hydrogen or fluorine;

and wherein said mol percent is based on the total amount of primary aromatic amines present.

DETAILS OF THE INVENTION

Herein certain terms are used and some of these are defined below.

By an "ortho position" is meant a position on an aryl group attached to an imino nitrogen, wherein the ortho position is a position adjacent to the position of the atom bound to the imino nitrogen atom. There are two such positions, a first position and a second position, one on "either side" of the position bonded to the imino nitrogen atom. In the present context these ortho positions will occur in groups $R^6$ and $R^7$. As illustrative examples these ortho positions are shown by asterisks in a phenyl ring [formula (IV)] and a 1-pyrrolyl ring [formula (V)].

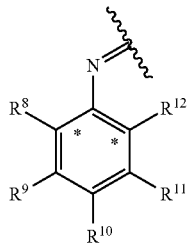

(IV)

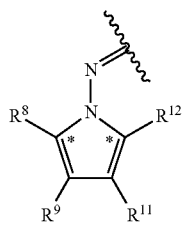

(V)

For syntheses of compounds in which 1-pyrrolyl groups are present, see U.S. Pat. No. 7,310,084, which is hereby included by reference.

By a "symmetrical diimine" is meant that the group bonded to the first ortho position in $R^6$ is the same as the group bonded to the first ortho position of $R^7$, and the group bonded to the second ortho position of $R^6$ is the same as the group bonded to the second ortho position of $R^7$. In other words, the diimine is symmetrical with respect to the groups bonded to the first and second ortho positions (excluding impurities). Groups bonded to other positions of these aryl groups may vary from $R^6$ to $R^7$, but in one preferred form, $R^6$ and $R^7$ are identical. When $R^6$ and $R^7$ are identical they are the same type of aryl group, i.e., phenyl or pyrrolyl, and the substituents on the aryl rings are the same and in the same positions.

By a "pyridine" is meant an aryl ring of Formula (VI), wherein $X^1$ and $X^2$ are independently carbon or nitrogen. It is preferred that both $X^1$ and $X^2$ are carbon.

By a "primary aromatic amine" or "primary arylamine" (PAA) is meant a primary amino group, —NH$_2$, bound directly to a ring atom of an aromatic ring. The amino group may be bound to a carbon atom, as in a benzene ring, or may be bound to another type of atom, such as a nitrogen atom at the one position of an pyrrole ring.

By "hydrocarbyl group" is meant a univalent group containing only carbon and hydrogen. If not otherwise stated, it is preferred that hydrocarbyl groups herein contain 1 to about 30 carbon atoms.

By "substituted hydrocarbyl" herein is meant a hydrocarbyl group that contains one or more substituent groups that are inert under the process conditions to which the compound containing these groups is subjected. The substituent groups also do not substantially interfere with the process. If not otherwise stated, it is preferred that substituted hydrocarbyl groups herein contain 1 to about 30 carbon atoms. Included in the meaning of "substituted" are heteroaromatic rings.

By "(inert) functional group" herein is meant a group other than hydrocarbyl or substituted hydrocarbyl that is inert under the process conditions to which the compound containing the group is subjected. The functional groups also do not substantially interfere with any process described herein that the compound in which they are present may take part. Examples of functional groups include halo (fluoro, chloro, bromo and iodo), ether such as —OR$^{18}$ wherein R$^{18}$ is hydrocarbyl or substituted hydrocarbyl. In cases where the functional group may be near an iron atom, the functional group should not coordinate to the iron atom more strongly than the groups the imino groups or nitrogen atom in the pyridine ring. That is inert functional groups should not displace the desired coordinating groups.

Preferred aryl groups for $R^6$ and $R^7$ are phenyl and 1-pyrrolyl, Formulas (VII) and (VIII) respectively, and phenyl is especially preferred.

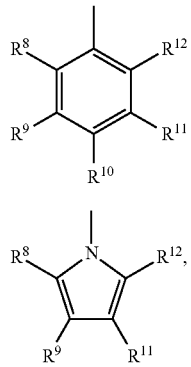

(VII)

(VIII)

wherein each $R^8$ is the same and is hydrocarbyl, substituted hydrocarbyl or a functional group, each $R^{12}$ is the same and is hydrogen or fluorine, and each $R^9$, $R^{10}$ and $R^{11}$ is independently hydrocarbyl, substituted hydrocarbyl, a functional group, or hydrogen.

To make α-olefins that are commercially valuable, typically $R^8$ is a group such as alkyl containing 1-6 carbon atoms, more preferably 1-4 carbon atoms, halo such as chloro or bromo (except fluorine), or a small functional group such as alkoxy such as methoxy containing 1 to 4 carbon atoms, while $R^{12}$ is typically hydrogen. This type of substitution pattern has the correct amount of steric hindrance to provide the desired α-olefins. However, in this synthesis of α-olefins the presence of small amounts of such diimines, which are more sterically hindered than the desired diimines, causes the formation of "excess" higher molecular weight products (higher olefins and polymers). For example, impurities in the PAA used to make the diimine may be substituted, in the case of (VII) and (VIII), by groups larger than hydrogen in the $R^{12}$ position.

The distribution of α-olefins produced by the present type of oligomerization catalyst usually follows the so-called Schulz-Flory equation (SFE). This measure of the molecular weights of the olefins obtained has a constant K (the Schulz-Flory constant, herein SFC) (see for instance B. Elvers, et al., Ed. Ullmann's Encyclopedia of Industrial Chemistry, Vol. A13, VCH Verlagsgesellschaft mnbH, Weinheim, 1989, p. 243-247 and 275-276). This is defined as:

$$K = n(C_{n+2}\ \text{olefin})/n(C_n\ \text{olefin})$$

wherein $n(C_n\ \text{olefin})$ is the number of moles of olefin containing n carbon atoms, and $n(C_{n+2}\ \text{olefin})$ is the number of moles of olefin containing n+2 carbon atoms, or in other words, the next higher oligomer of $C_n$ olefin. From this can be determined the weight (mass) fractions of the various olefins in the resulting oligomeric reaction product mixture.

The following illustration of the effect of such larger substituted aryl groups, $R^6$ and $R^7$, on the product distribution is based on a diimine in which $R^1$ to $R^3$ are hydrogen. $X^1$ and $X^2$ are carbon, $R^4$ and $R^5$ are methyl, and $R^6$ and $R^7$ are (VII) in which $R^8$ is methyl and $R^9$ to $R^{12}$ are hydrogen. This diimine is readily made from by the reaction of o-toluidine with 2,6-diacetylpyridine (see U.S. Pat. No. 6,103,946). However, if there is small amount of 2,6-dimethylaniline in the o-toluidine, a diimine in which a small amount of $R^{12}$ is methyl in the $R^6$ group will be present, and an even smaller amount of diimine in which the $R^{12}$ groups in $R^6$ and $R^7$ are both methyl will be present. As shown below, this has a profound effect on the amount of higher MW product produced.

For the purposes of this illustration it is assumed that the o-toluidine used has 0.5 mole percent of 2,6-dimethylaniline as an impurity. This in turn means that 0.5 mole percent of the diimine produced by reaction with 2,6-diacetylpyridine will have an $R^6$ group in which both $R^8$ and $R^{12}$ are methyl (in the $R^7$ group $R^8$ is methyl and $R^{12}$ is hydrogen). The SFC for the diimine in which 2 ortho methyl groups are present is approximately 0.65, while the SFC for the diimine in which 3 ortho methyl groups are present is about 0.86. Using the SFE we can construct a table in which the weight fraction of each olefin generated by these two diimines. This is shown in Table 1 for olefins having 4 to 200 carbon atoms. It is assumed for these calculations that only olefins containing 200 carbons or less are produced, and although this is not strictly speaking true, the approximation does not appreciably affect the results.

TABLE 1

| SF Constant | | 0.65 | | | | 0.86 | | | |
| --- | --- | --- | --- | --- | --- | --- | --- | --- | --- |
| Column No. | 1 | 2 | 3 | 4 | 5 | 6 | 7 | 8 | 9 | 10 |
| No. Olefin C | MW | Mole % | | Wt % | | Mole % | | Wt % | Combined Wt. % |
| 4  | 58  | 1.0000 | 35.0 | 2030.0 | 18.841864 | 1.0000 | 14.0 | 812.0  | 3.570980 | 18.765509 |
| 6  | 84  | 0.6500 | 22.8 | 1911.0 | 17.737340 | 0.8600 | 12.0 | 1011.4 | 4.447718 | 17.670892 |
| 8  | 112 | 0.4225 | 14.8 | 1656.2 | 15.372362 | 0.7396 | 10.4 | 1159.7 | 5.100049 | 15.321000 |
| 10 | 130 | 0.2746 | 9.6  | 1249.5 | 11.597898 | 0.6361 | 8.9  | 1157.6 | 5.090942 | 11.565363 |
| 12 | 168 | 0.1785 | 6.2  | 1049.6 | 9.742234  | 0.5470 | 7.7  | 1286.6 | 5.657995 | 9.721813 |
| 14 | 196 | 0.1160 | 4.1  | 796.0  | 7.387861  | 0.4704 | 6.6  | 1290.9 | 5.676855 | 7.379306 |
| 16 | 224 | 0.0754 | 2.6  | 591.3  | 5.488125  | 0.4046 | 5.7  | 1268.7 | 5.579537 | 5.488582 |
| 18 | 252 | 0.0490 | 1.7  | 432.4  | 4.013192  | 0.3479 | 4.9  | 1227.5 | 5.398202 | 4.020117 |
| 20 | 280 | 0.0319 | 1.1  | 312.3  | 2.898416  | 0.2992 | 4.2  | 1172.9 | 5.158282 | 2.909716 |
| 22 | 308 | 0.0207 | 0.7  | 223.3  | 2.072368  | 0.2573 | 3.6  | 1109.6 | 4.879735 | 2.086404 |
| 24 | 336 | 0.0135 | 0.5  | 158.3  | 1.469497  | 0.2213 | 3.1  | 1041.0 | 4.578079 | 1.485040 |
| 26 | 364 | 0.0088 | 0.3  | 111.5  | 1.034771  | 0.1903 | 2.7  | 969.9  | 4.265243 | 1.050923 |
| 28 | 392 | 0.0057 | 0.2  | 78.0   | 0.724340  | 0.1637 | 2.3  | 898.2  | 3.950272 | 0.740469 |
| 30 | 420 | 0.0037 | 0.1  | 54.3   | 0.504451  | 0.1408 | 2.0  | 827.7  | 3.639893 | 0.520128 |
| 32 | 448 | 0.0024 | 0.1  | 37.7   | 0.349753  | 0.1211 | 1.7  | 759.2  | 3.338995 | 0.364699 |
| 34 | 476 | 0.0016 | 0.1  | 26.0   | 0.241548  | 0.1041 | 1.5  | 693.8  | 3.051007 | 0.255595 |
| 36 | 504 | 0.0010 | 0.0  | 17.9   | 0.166242  | 0.0895 | 1.3  | 631.7  | 2.778211 | 0.179302 |

TABLE 1-continued

| SF Constant | | | 0.65 | | | | 0.86 | | | |
|---|---|---|---|---|---|---|---|---|---|---|
| Column No.<br>No. Olefin C | 1<br>MW | 2 | 3<br>Mole % | 4 | 5<br>Wt % | 6 | 7<br>Mole % | 8 | 9<br>Wt % | 10<br>Combined Wt. % |
| 38 | 532 | 0.0007 | 0.0 | 12.3 | 0.114060 | 0.0770 | 1.1 | 573.5 | 2.521998 | 0.126100 |
| 40 | 560 | 0.0004 | 0.0 | 8.4 | 0.078041 | 0.0662 | 0.9 | 519.1 | 2.283072 | 0.089066 |
| 42 | 588 | 0.0003 | 0.0 | 5.7 | 0.053263 | 0.0569 | 0.8 | 468.8 | 2.061614 | 0.063305 |
| 44 | 616 | 0.0002 | 0.0 | 3.9 | 0.036270 | 0.0490 | 0.7 | 422.4 | 1.857416 | 0.045375 |
| 46 | 644 | 0.0001 | 0.0 | 2.7 | 0.024647 | 0.0421 | 0.6 | 379.7 | 1.669986 | 0.032874 |
| 48 | 672 | 0.0001 | 0.0 | 1.8 | 0.016717 | 0.0362 | 0.5 | 340.8 | 1.498631 | 0.024127 |
| 50 | 700 | 0.0000 | 0.0 | 1.2 | 0.011319 | 0.0312 | 0.4 | 305.3 | 1.342523 | 0.017975 |
| 52 | 728 | 0.0000 | 0.0 | 0.8 | 0.007652 | 0.0268 | 0.4 | 273.0 | 1.200753 | 0.013617 |
| 54 | 756 | 0.0000 | 0.0 | 0.6 | 0.005165 | 0.0230 | 0.3 | 243.8 | 1.072365 | 0.010501 |
| 56 | 784 | 0.0000 | 0.0 | 0.4 | 0.003481 | 0.0198 | 0.3 | 217.5 | 0.956391 | 0.008246 |
| 58 | 812 | 0.0000 | 0.0 | 0.3 | 0.002344 | 0.0170 | 0.2 | 193.7 | 0.851871 | 0.006591 |
| 60 | 840 | 0.0000 | 0.0 | 0.2 | 0.001576 | 0.0147 | 0.2 | 172.3 | 0.757871 | 0.005357 |
| 62 | 868 | 0.0000 | 0.0 | 0.1 | 0.001059 | 0.0126 | 0.2 | 153.1 | 0.673495 | 0.004421 |
| 64 | 896 | 0.0000 | 0.0 | 0.1 | 0.000710 | 0.0108 | 0.2 | 136.0 | 0.597890 | 0.003696 |
| 66 | 924 | 0.0000 | 0.0 | 0.1 | 0.000476 | 0.0093 | 0.1 | 120.6 | 0.530253 | 0.003125 |
| 68 | 952 | 0.0000 | 0.0 | 0.0 | 0.000319 | 0.0080 | 0.1 | 106.8 | 0.469837 | 0.002666 |
| 70 | 980 | 0.0000 | 0.0 | 0.0 | 0.000213 | 0.0069 | 0.1 | 94.6 | 0.415944 | 0.002292 |
| 72 | 1008 | 0.0000 | 0.0 | 0.0 | 0.000143 | 0.0059 | 0.1 | 83.7 | 0.367932 | 0.001982 |
| 74 | 1036 | 0.0000 | 0.0 | 0.0 | 0.000095 | 0.0051 | 0.1 | 73.9 | 0.325211 | 0.001721 |
| 76 | 1064 | 0.0000 | 0.0 | 0.0 | 0.000064 | 0.0044 | 0.1 | 65.3 | 0.287240 | 0.001499 |
| 78 | 1092 | 0.0000 | 0.0 | 0.0 | 0.000042 | 0.0038 | 0.1 | 57.6 | 0.253527 | 0.001310 |
| 80 | 1120 | 0.0000 | 0.0 | 0.0 | 0.000028 | 0.0032 | 0.0 | 50.8 | 0.223624 | 0.001146 |
| 82 | 1148 | 0.0000 | 0.0 | 0.0 | 0.000019 | 0.0028 | 0.0 | 44.8 | 0.197125 | 0.001004 |
| 84 | 1176 | 0.0000 | 0.0 | 0.0 | 0.000013 | 0.0024 | 0.0 | 39.5 | 0.173662 | 0.000881 |
| 86 | 1204 | 0.0000 | 0.0 | 0.0 | 0.000008 | 0.0021 | 0.0 | 34.8 | 0.152905 | 0.000773 |
| 88 | 1232 | 0.0000 | 0.0 | 0.0 | 0.000006 | 0.0018 | 0.0 | 30.6 | 0.134557 | 0.000678 |
| 90 | 1260 | 0.0000 | 0.0 | 0.0 | 0.000004 | 0.0015 | 0.0 | 26.9 | 0.118349 | 0.000595 |
| 92 | 1288 | 0.0000 | 0.0 | 0.0 | 0.000002 | 0.0013 | 0.0 | 23.7 | 0.104042 | 0.000523 |
| 94 | 1316 | 0.0000 | 0.0 | 0.0 | 0.000002 | 0.0011 | 0.0 | 20.8 | 0.091421 | 0.000459 |
| 96 | 1344 | 0.0000 | 0.0 | 0.0 | 0.000001 | 0.0010 | 0.0 | 18.3 | 0.080295 | 0.000403 |
| 98 | 1372 | 0.0000 | 0.0 | 0.0 | 0.000001 | 0.0008 | 0.0 | 16.0 | 0.070492 | 0.000353 |
| 100 | 1400 | 0.0000 | 0.0 | 0.0 | 0.000000 | 0.0007 | 0.0 | 14.1 | 0.061860 | 0.000310 |
| 102 | 1428 | 0.0000 | 0.0 | 0.0 | 0.000000 | 0.0006 | 0.0 | 12.3 | 0.054264 | 0.000272 |
| 104 | 1456 | 0.0000 | 0.0 | 0.0 | 0.000000 | 0.0005 | 0.0 | 10.8 | 0.047582 | 0.000238 |
| 106 | 1484 | 0.0000 | 0.0 | 0.0 | 0.000000 | 0.0005 | 0.0 | 9.5 | 0.041708 | 0.000209 |
| 108 | 1512 | 0.0000 | 0.0 | 0.0 | 0.000000 | 0.0004 | 0.0 | 8.3 | 0.036545 | 0.000183 |
| 110 | 1540 | 0.0000 | 0.0 | 0.0 | 0.000000 | 0.0003 | 0.0 | 7.3 | 0.032011 | 0.000160 |
| 112 | 1568 | 0.0000 | 0.0 | 0.0 | 0.000000 | 0.0003 | 0.0 | 6.4 | 0.028030 | 0.000140 |
| 114 | 1596 | 0.0000 | 0.0 | 0.0 | 0.000000 | 0.0002 | 0.0 | 5.6 | 0.024536 | 0.000123 |
| 116 | 1624 | 0.0000 | 0.0 | 0.0 | 0.000000 | 0.0002 | 0.0 | 4.9 | 0.021471 | 0.000107 |
| 118 | 1652 | 0.0000 | 0.0 | 0.0 | 0.000000 | 0.0002 | 0.0 | 4.3 | 0.018784 | 0.000094 |
| 120 | 1680 | 0.0000 | 0.0 | 0.0 | 0.000000 | 0.0002 | 0.0 | 3.7 | 0.016428 | 0.000082 |
| 122 | 1708 | 0.0000 | 0.0 | 0.0 | 0.000000 | 0.0001 | 0.0 | 3.3 | 0.014363 | 0.000072 |
| 124 | 1736 | 0.0000 | 0.0 | 0.0 | 0.000000 | 0.0001 | 0.0 | 2.9 | 0.012555 | 0.000063 |
| 126 | 1764 | 0.0000 | 0.0 | 0.0 | 0.000000 | 0.0001 | 0.0 | 2.5 | 0.010971 | 0.000055 |
| 128 | 1792 | 0.0000 | 0.0 | 0.0 | 0.000000 | 0.0001 | 0.0 | 2.2 | 0.009585 | 0.000048 |
| 130 | 1820 | 0.0000 | 0.0 | 0.0 | 0.000000 | 0.0001 | 0.0 | 1.9 | 0.008372 | 0.000042 |
| 132 | 1848 | 0.0000 | 0.0 | 0.0 | 0.000000 | 0.0001 | 0.0 | 1.7 | 0.007311 | 0.000037 |
| 134 | 1876 | 0.0000 | 0.0 | 0.0 | 0.000000 | 0.0001 | 0.0 | 1.5 | 0.006383 | 0.000032 |
| 136 | 1904 | 0.0000 | 0.0 | 0.0 | 0.000000 | 0.0000 | 0.0 | 1.3 | 0.005571 | 0.000028 |
| 138 | 1932 | 0.0000 | 0.0 | 0.0 | 0.000000 | 0.0000 | 0.0 | 1.1 | 0.004861 | 0.000024 |
| 140 | 1960 | 0.0000 | 0.0 | 0.0 | 0.000000 | 0.0000 | 0.0 | 1.0 | 0.004241 | 0.000021 |
| 142 | 1988 | 0.0000 | 0.0 | 0.0 | 0.000000 | 0.0000 | 0.0 | 0.8 | 0.003700 | 0.000018 |
| 144 | 2016 | 0.0000 | 0.0 | 0.0 | 0.000000 | 0.0000 | 0.0 | 0.7 | 0.003227 | 0.000016 |
| 146 | 2044 | 0.0000 | 0.0 | 0.0 | 0.000000 | 0.0000 | 0.0 | 0.6 | 0.002813 | 0.000014 |
| 148 | 2072 | 0.0000 | 0.0 | 0.0 | 0.000000 | 0.0000 | 0.0 | 0.6 | 0.002453 | 0.000012 |
| 150 | 2100 | 0.0000 | 0.0 | 0.0 | 0.000000 | 0.0000 | 0.0 | 0.5 | 0.002138 | 0.000011 |
| 152 | 2128 | 0.0000 | 0.0 | 0.0 | 0.000000 | 0.0000 | 0.0 | 0.4 | 0.001863 | 0.000009 |
| 154 | 2156 | 0.0000 | 0.0 | 0.0 | 0.000000 | 0.0000 | 0.0 | 0.4 | 0.001623 | 0.000008 |
| 156 | 2184 | 0.0000 | 0.0 | 0.0 | 0.000000 | 0.0000 | 0.0 | 0.3 | 0.001414 | 0.000007 |
| 158 | 2212 | 0.0000 | 0.0 | 0.0 | 0.000000 | 0.0000 | 0.0 | 0.3 | 0.001232 | 0.000006 |
| 160 | 2240 | 0.0000 | 0.0 | 0.0 | 0.000000 | 0.0000 | 0.0 | 0.2 | 0.001073 | 0.000005 |
| 162 | 2268 | 0.0000 | 0.0 | 0.0 | 0.000000 | 0.0000 | 0.0 | 0.2 | 0.000934 | 0.000005 |
| 164 | 2296 | 0.0000 | 0.0 | 0.0 | 0.000000 | 0.0000 | 0.0 | 0.2 | 0.000813 | 0.000004 |
| 166 | 2324 | 0.0000 | 0.0 | 0.0 | 0.000000 | 0.0000 | 0.0 | 0.2 | 0.000708 | 0.000004 |
| 168 | 2352 | 0.0000 | 0.0 | 0.0 | 0.000000 | 0.0000 | 0.0 | 0.1 | 0.000616 | 0.000003 |
| 170 | 2380 | 0.0000 | 0.0 | 0.0 | 0.000000 | 0.0000 | 0.0 | 0.1 | 0.000536 | 0.000003 |
| 172 | 2408 | 0.0000 | 0.0 | 0.0 | 0.000000 | 0.0000 | 0.0 | 0.1 | 0.000467 | 0.000002 |
| 174 | 2436 | 0.0000 | 0.0 | 0.0 | 0.000000 | 0.0000 | 0.0 | 0.1 | 0.000406 | 0.000002 |
| 176 | 2464 | 0.0000 | 0.0 | 0.0 | 0.000000 | 0.0000 | 0.0 | 0.1 | 0.000353 | 0.000002 |
| 178 | 2492 | 0.0000 | 0.0 | 0.0 | 0.000000 | 0.0000 | 0.0 | 0.1 | 0.000307 | 0.000002 |
| 180 | 2520 | 0.0000 | 0.0 | 0.0 | 0.000000 | 0.0000 | 0.0 | 0.1 | 0.000267 | 0.000001 |
| 182 | 2548 | 0.0000 | 0.0 | 0.0 | 0.000000 | 0.0000 | 0.0 | 0.1 | 0.000232 | 0.000001 |
| 184 | 2576 | 0.0000 | 0.0 | 0.0 | 0.000000 | 0.0000 | 0.0 | 0.0 | 0.000202 | 0.000001 |
| 186 | 2604 | 0.0000 | 0.0 | 0.0 | 0.000000 | 0.0000 | 0.0 | 0.0 | 0.000176 | 0.000001 |

TABLE 1-continued

| SF Constant | | 0.65 | | | | 0.86 | | | |
|---|---|---|---|---|---|---|---|---|---|
| Column No. | 1 | 2 | 3 | 4 | 5 | 6 | 7 | 8 | 9 | 10 |
| No. Olefin C | MW | Mole % | | Wt % | | Mole % | | Wt % | | Combined Wt. % |
| 188 | 2632 | 0.0000 | 0.0 | 0.0 | 0.000000 | 0.0000 | 0.0 | 0.0 | 0.000153 | 0.000001 |
| 190 | 2660 | 0.0000 | 0.0 | 0.0 | 0.000000 | 0.0000 | 0.0 | 0.0 | 0.000133 | 0.000001 |
| 192 | 2688 | 0.0000 | 0.0 | 0.0 | 0.000000 | 0.0000 | 0.0 | 0.0 | 0.000115 | 0.000001 |
| 194 | 2716 | 0.0000 | 0.0 | 0.0 | 0.000000 | 0.0000 | 0.0 | 0.0 | 0.000100 | 0.000001 |
| 196 | 2744 | 0.0000 | 0.0 | 0.0 | 0.000000 | 0.0000 | 0.0 | 0.0 | 0.000087 | 0.000000 |
| 198 | 2772 | 0.0000 | 0.0 | 0.0 | 0.000000 | 0.0000 | 0.0 | 0.0 | 0.000076 | 0.000000 |
| 200 | 2800 | 0.0000 | 0.0 | 0.0 | 0.000000 | 0.0000 | 0.0 | 0.0 | 0.000066 | 0.000000 |
| Sums | | 2.8571 | | 10773.9 | | 7.1429 | | 22738.9 | | |

The calculations for Table 1 are quite simple. Column 2, in accordance with the SFE starts with one, and the next value is the previous value in column 2 multiplied by the SFC. These are then summed, and then each value in column 2 is divided by the sum of column 2 and entered in column 3. Column 3 is than multiplied by the MW of the olefin (column 1) and entered in column 4. Column 4 is than summed, and each value in column 4 is divided by the sum of column 4 and multiplied by 100 to get the weight percent of each olefin, entered in column 5. The calculations for columns 6-9 are analogous. To get the combined weight percent for diimine mixture of 99.5 mol percent with a SFC of 0.65 and 0.5 mole % with a SFC of 0.85, multiply column 5 by 0.995 and column 9 by 0.005 and sum them. This sum is shown in column 10. All of the calculations in this illustration assume that (i) all of the iron complexes oligomerize/polymerize ethylene at the same rate and (ii) the rate of imine formation for o-toluidine and 2,6-dimethylaniline is the same.

For the purposes of this illustration we have arbitrarily chosen olefins having 100-200 carbon atoms as materials that may precipitate and foul the reaction system. The larger the number of carbon atoms in the olefin the higher the melting point. At a SFC of 0.65, the weight percent of such olefins is <0.000000; at a SFC of 0.86 the weight percent is 0.495714; and the combined diimines it is 0.002480 weight percent. While this does not seem like much, in a large scale manufacturing plant it represents a significant amount that can foul the reaction system walls. For a plant producing 250,000,000 kg/year this would mean the combined diimines would produce 6,200 kg of olefins having 100-200 carbon atoms, a significant amount to foul process surfaces and in some instances perhaps even clog pipes or pumps. Using similar calculations, the amount of $C_{100}$-$C_{200}$ olefins produced at various levels of a diimine with a SFC of 0.86 is shown in Table 2.

TABLE 2

| Mole % SFC 0.86 | kg $C_{100}$-$C_{200}$/250,000,000 kg product |
|---|---|
| 0.01 | 128 |
| 0.05 | 623 |
| 0.1 | 1243 |
| 0.5 | 6200 |
| 1.0 | 12398 |
| 2.0 | 24790 |

The presence of the 2,6-dimethylaniline also causes problems because very small amounts tetramethyl-substituted diimine will also be produced by reaction of 2 molecules of 2,6-dimethylaniline with a molecule of 2,6-diacetyl pyridine. Although the mole fraction of this diimine will be very low (it is approximately the mole fraction of the 2,6-dimethylaniline squared), it is significant because it is well known that this diimine with 4 aryl methyl groups produces only high MW polyethylene (see U.S. Pat. No. 5,886,663). Thus by similar calculations we can estimate the amount of polyethylene produced by similar calculations, and the results are shown in Table 3.

TABLE 3

| Mole % 2,6-Dimethylaniline | Mole Fraction Tetrasubstituted Catalyst | kg Polymer/250,000,000 kg Product |
|---|---|---|
| 0.01 | 0.00000001 | 2.5 |
| 0.05 | 0.00000025 | 62.5 |
| 0.1 | 0.000001 | 250 |
| 0.5 | 0.000025 | 6250 |
| 1 | 0.0001 | 25000 |
| 2 | 0.0004 | 100000 |

Thus the total amount of high MW products formed at various 2.4-dimethylaniline concentrations are shown in Table 4.

TABLE 4

| Mole % 2,6-Dimethylaniline | kg high MW/250,000,000 kg Product |
|---|---|
| 0.01 | 131 |
| 0.05 | 686 |
| 0.1 | 1493 |
| 0.5 | 12450 |
| 1 | 37348 |
| 2 | 124970 |

The amount of high MW products goes up very rapidly as the amount of 2,4-dimethylaniline goes to above 0.5 mol percent, principally because the amount of polymer being produced is going up very rapidly.

To provide an iron complex of (III) with requisite purity, a couple of approaches may be taken. The ligand itself [(III)], if a solid, may be purified by crystallization, or the iron complex may similarly be purified. However since the impurities differ from the desired material by only a few atoms, such a purification may be difficult and may result large losses of desired iron complex. A preferred approach is to start with as pure a PAA as possible. Such an approach is illustrated below for o-toluidine.

o-Toluidine is made by the reduction of 2-methylnitrobenzene, which in turn is made by nitration of toluene. Similarly, the impurity 2,6-dimethylaniline arises by the reduction of 2,6-dimethylnitrobenzene, which in turn is made by the nitration of m-xylene (another product of this nitration is 2,4-dimethylnitrobenzene). Boiling points from the literature of compounds of interest are given below in Table 5.

TABLE 5

| Compound | b.p., ° C. |
|---|---|
| toluene | 111 |
| m-xylene | 139 |
| 2-methylnitrobenzene | 225 |
| 3-methylnitrobenzene | 230-231 |
| 4-methylnitrobenzene | 238 |
| o-toluidine | 199-200 |
| m-toluidine | 203-204 |
| p-toluidine | 200 |
| 2,6-dimethylaniline | 214 |

As can be seen from Table 5, the easiest way of avoiding 2,6-dimethylaniline in the o-toluidine is to carefully distill the toluene used in the nitration step, to eliminate the m-xylene (and also o- and p-xylene). This can be readily accomplished, although it is not apparently so carefully done for so-called nitration grade toluene, which usually does contain some xylenes. If there is no m-xylene in the starting toluene, it is essentially impossible to obtain 2,6-dimethylaniline impurity using this synthetic method.

In addition there are other reasons for not having other PAA impurities. For instance if m- and/or p-toluidine are present they will give iron complex derived from the "mixed" diimine in which $R^6$ has one ortho methyl group and $R^7$ has no ortho methyl group (it is either meta or para), and these compounds are less sterically hindered than the desired complex, and therefore will give "excess" lower MW AOs (see U.S. Pat. No. 6,710,006, FIGS. 1 and 2, where excess lower MW olefins also appear to be present). While not as deleterious as higher MW products (they normally will not solidify in the product stream), 1-butene in particular has a relatively low value, and so is not desirable as a product.

From the boiling points it can be seen that a good method of removing any p-toluidine from the o-toluidine is to carefully separate the corresponding nitrobenzenes by distillation. m-Nitrobenzene may also be so separated, but its boiling point is close to that of the ortho isomer. However using the proper nitration conditions the amount of m-nitrobenzene produced may be minimized.

By using analogous methods, using differences in boiling points of the PAA or any of its intermediates, and perhaps crystallization when the arylamine or any intermediates are solids, pure PAAs, especially those not having substituents in the second ortho position, may be produced. In some cases the pure PAAs may be commercially available, for example o-toluidine reported to be ≥95.5% pure is available from Sigma-Aldrich Corp. (St. Louis, Mo. 63103, USA) as Fluka #89610. This material is reported to typically have about 0.2-03 mol percent of m- and p-toluidine present, and no 2,6-dimethylaniline present.

It is preferred that the desired PAA to be used in the synthesis be at least about 99.0 mol percent of the PAAs present in the material, more preferably at least about 99.5 mol percent, and very preferably at about 99.7 mol percent.

A symmetrical diimine of a 2,6-diacylpyridine or a 2,6-pyridinedicarboxaldehyde should be made with a PAA that contains no more than 0.5 mol percent, preferably no more than about 0.3 mole percent, more preferably no more than about 0.2 mol percent, and very preferably no more than about 0.1 mol percent of impurities, which impurities are themselves PAAs and in which one of the second ortho positions is not hydrogen or fluorine. It is to be understood that any required or preferred maximum level of such amines may be combined with any of the minimum overall purities for the PAA in the immediately preceding paragraph to form a pair of preferred "specifications" (limitations) on the purity of the PAA and/or the resulting final ligand and/or final iron complex, as well as the use of iron ligand in the oligomerization process.

The purity of the PAA used to synthesize the ligand and subsequently the iron complex may be determined by gas chromatography (GC) using standard GC procedures. Using o-toluidine again as an illustration, see for instance Ray A. Dove, *Analytical Chemistry*, vol. 39, p. 1188-1190 (1967) in which the analysis of various aromatic amines is done (which in the present context such aromatic amines may be desired or undesirable impurities) by GC of the trifluoroacetyl derivatives. Derivatization is not necessary, see for instance J. S. Parsons, et al., *Analytical Chemistry*, vol. 36, p. 237-238 (1964). For PAAs or impurities not specifically mentioned in these papers, routine changes may be made to the procedures described to carry out the needed analysis. These changes may include changing the column packing, temperature, or temperature profile, etc. To a first approximation (see Dove) the response of detectors is typically the same for similar compounds, so to a first approximation the area percent of the eluate compared to the total area of the arylamines present will give an approximate value of the mole percent (doing the appropriate calculations) of any particular arylamine present. For more exact determination of mol percents of compounds present, relative response factors may be determined and used in the calculations a standard way (see Dove). GC is a relatively old and well known analytical method, and analyses such as these are well known. If applicable, the method of Dove, or a close analog, is preferred (Dove calculated weight percents, but these are easily converted to mol percents of the total arylamines present). By a close analog, for instance, the Dove method may be used but for less volatile arylamines, the temperature of the column may be held for a while at 152° C. and then ramped up slowly to a higher temperature.

In order to analyze ligands or complexes in which the ligands or complex is already fully formed, the ligand or complex (0.5-1.0 g) is placed in a solution of p-toluenesulfonic acid (0.5-1.0 g) in solution of 10 ml of ethanol and 3 ml of water. None of these amounts is critical but there must be enough water to hydrolyze the imino groups, preferably a large excess of water, and enough p-toluenesulfonic acid to form salts with the arylamines formed. The mixture is then heated and shaken or stirred in a bomb at 200° C. for 4 hours. Then 10 ml of water is added to the resulting material, which is neutralized to pH 9 with sodium carbonate solution and extracted several times with ethyl ether. The ethyl ether extracts are concentrated (care should be taken not to remove much less volatile material, such as arylamines), and then the concentrate is analyzed by GC for the arylamines present. The GC may be combined with mass spectroscopy to identify the various materials eluted. Appropriate standards are used to calibrate the GC, both for the relative retention time and responses of the various components. Calculation of the mol percent of the various arylamines are carried out as described above.

Although this invention has been described in connection with specific forms thereof, it should be appreciated that a wide array of equivalents may be substituted for the specific elements shown and described herein without departing from the spirit and scope of this invention as described in the appended claims.

What is claimed is:

1. An improved process for the oligomerization of ethylene to provide a series of α-olefins of formula $CH_2$=$CH_2$ $(CH_2CH_2)_nH$ wherein n is an integer of 1 or more, in the presence of a catalyst system comprising an iron complex of a symmetrical diimine of a 2,6-diacylpyridine or a 2,6-pyridinedicarboxaldehyde of the formula

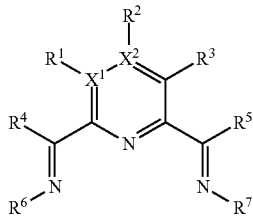

(III)

wherein:
- $X^1$ and $X^2$ are each independently carbon or nitrogen;
- $R^1$ and $R^2$ are independently hydrogen, hydrocarbyl, substituted hydrocarbyl or a functional group, provided that when $X^1$ is nitrogen $R^1$ is not present, and when $X^2$ is nitrogen $R^2$ is not present;
- $R^3$ is hydrocarbyl, substituted hydrocarbyl, a functional group or hydrogen;
- $R^4$ and $R^5$ are each independently hydrogen, hydrocarbyl, or substituted hydrocarbyl;
- $R^6$ and $R^7$ are the same, and are aryl groups in which a first ortho position is substituted by hydrocarbyl, substituted hydrocarbyl or a functional group, and a second ortho position is hydrogen or fluorine;

wherein the improvement comprises:
- said symmetrical diimine of a 2,6-diacylpyridine or a 2,6-pyridinedicarboxaldehyde is made with a primary aromatic amine which contains no more than 0.5 mol percent of impurities which are themselves primary aromatic amines and in which one of said second ortho positions is not hydrogen or fluorine;

and/or
- said symmetrical diimine of a 2,6-diacylpyridine or a 2,6-pyridinedicarboxaldehyde contains no more than 0.5 mol percent of diimines in which said one of said second ortho positions is not a hydrogen or fluorine;
- and wherein said mol percent is based on the total amount of primary aromatic amines present.

2. The process as recited in claim 1 wherein $X^1$ and $X^2$ are carbon and $R^1$, $R^2$ and $R^3$ are hydrogen.

3. The process as recited in claim 2 wherein said $R^4$ and $R^5$ are the same and are hydrogen or methyl.

4. The process as recited in claim 3 wherein $R^6$ and $R^7$ are

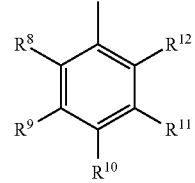

(VII)

wherein:
- $R^8$ is hydrocarbyl, substituted hydrocarbyl, or a functional group;
- $R^9$, $R^{10}$, and $R^{11}$ are hydrogen hydrocarbyl, substituted hydrocarbyl or a functional group; and
- $R^{12}$ is hydrogen or fluorine.

5. The process as recited in claim 4 wherein $R^8$ is alkyl containing 1 to 4 carbon atoms, chloro, bromo, or alkoxy containing one to four carbon atoms.

6. The process as recited claim 1 wherein said symmetrical diimine of a 2,6-diacylpyridine or a 2,6-pyridinedicarboxaldehyde is made with said primary aromatic amine which contains no more than 0.1 mol percent of impurities which are themselves primary aromatic amines and in which one of said second ortho positions is not hydrogen or fluorine.

7. The process as recited claim 1 wherein said symmetrical diimine of a 2,6-diacylpyridine or a 2,6-pyridinedicarboxaldehyde is made with a primary aromatic amine which contains no more than 0.5 mol percent of impurities which are themselves primary aromatic amines and in which one of said second ortho positions is not hydrogen or fluorine.

8. The process as recited in claim 1, wherein said symmetrical diimine of a 2,6-diacylpyridine or a 2,6-pyridinedicarboxaldehyde is made with said primary aromatic amine which contains no more than 0.1 mol percent of impurities which are themselves primary aromatic amines and in which one of said second ortho positions is not hydrogen or fluorine.

* * * * *